United States Patent [19]
Garzia

[11] 3,968,233
[45] July 6, 1976

[54] α-AMINO-γ-BUTYROLACTONES AS SEDATIVES

[75] Inventor: Aldo Garzia, Milan, Italy

[73] Assignee: Istituto Chemioterapico Italiano, Milan, Italy

[22] Filed: Aug. 6, 1975

[21] Appl. No.: 602,163

Related U.S. Application Data

[62] Division of Ser. No. 421,899, Dec. 5, 1973, abandoned.

[52] U.S. Cl. .............................. 424/279; 260/343.6
[51] Int. Cl.² ................ A61K 31/34; A61K 31/365
[58] Field of Search .................. 260/343.6; 424/279

[56] References Cited
FOREIGN PATENTS OR APPLICATIONS
791M 9/1961 France ................................ 424/27

OTHER PUBLICATIONS
Plieninger, Berichte, vol. 83, pp. 268–271, (1950).

Krattz et al., Liebigs Ann. Chem., vol. 744, pp. 33–41, (1971).
Sugano, Bulletin Chemical Society of Japan, vol. 83, pp. 669–670, (1973).

Primary Examiner—Jerome D. Goldberg
Assistant Examiner—Vera C. Clarke
Attorney, Agent, or Firm—Robert H. Dewey; Howard E. Post

[57] ABSTRACT

Compounds corresponding to the formula:

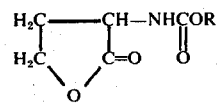

where R is an alkyl group of 3 to 5 carbon atoms are anticonvulsants and sedatives.

5 Claims, No Drawings

α-AMINO-γ-BUTYROLACTONES AS SEDATIVES

This is a division of copending application Ser. No. 421,899, filed Dec. 5, 1973, now abandoned.

BACKGROUND OF THE INVENTION

This invention relates to alkyl carbamate derivatives of α-amino-γ-butyrolactone. In a particular aspect, this invention relates to alkyl carbamate derivatives of α-amino-γ-butyrolactones having anti-convulsant, anti-epileptic and sedative active in mammals.

Many anti-convulsant agents and sedatives are available to the physician. Yet most, if not all, suffer from some disadvantage or other. The may have undesirable side effects, or may be habit-forming. Some patients may develop an allergic reaction. Accordingly there is a need for additional anti-convulsant agents and sedatives in the physicians armamentarium.

SUMMARY OF THE INVENTION

It is an object of this invention to provide alkyl carbamate derivatives of α-amino-γ-butyrolactone.

It is another object of this invention to provide a method of depressing the activity of the central nervous system of a living animal body.

It is yet another object of this invention to provide a method of treating epilepsy, insomnia and other disorders of the central nervous system which respond to anticonvulsant agents and sedatives.

Other objects will be apparent to those skilled in the art from the disclosure herein.

It is the discovery of this invention to provide alkyl carbamate derivatives of α-amino-γ-butyrolactone, and process for preparing same, represented by the formula $$\begin{array}{c} H_2C\text{————}CH\text{—}NHCOR \\ | \quad\quad\quad | \quad\quad\quad \| \\ H_2C \quad\quad C{=}O \quad\quad O \\ \backslash \quad\quad / \\ O \end{array}$$

where R is an alkyl group of 3–5 carbon atoms. These compounds have anti-convulsant, anti-epileptic, and sedative activity when administered to mammals.

DETAILED DESCRIPTION

The α-amino-γ-butyrolactone derivatives of the present invention include
- α-n-butoxycarbonyl-amino-γ-butyrolactone
- α-n-propoxycarbonyl-amino-γ-butyrolactone
- α-iso-propoxycarbonyl-amino-γ-butyrolactone
- α-iso-butoxycarbonyl-amino-γ-butyrolactone
- α-tert-butoxycarbonyl-amino-γ-butyrolactone
- α-n-pentoxycarbonyl-amino-γ-butyrolactone The preferred compound is α-n-butoxycarbonyl-amino-γ-butyrolactone, hereinafter designated AP-28.

These compounds, and especially AP-28, can be conveniently administered orally or intraperitoneally in doses of from about 200 to about 2000 mg/kg depending on the effect desired. In some extreme cases, doses higher than 2000 mg/kg may be indicated. The selection of the proper dosage is well within the ability of one of ordinary skill in the art and it is not intended that the invention be limited thereby. AP-28 is generally more effective when administered intraperitoneally than orally and smaller doses can be administered to achieve a given effect. However oral administration is more convenient and more acceptable to the patient and therefore is the preferred mode. Generally the preferred oral dose is 500 to 1500 mg/kg.

The compounds of the present invention are generally prepared by reacting the corresponding alkyl chloroformate with α-amino-γ-butyrolactone at reduced temperatures and in the presence of pyridine. α-Amino-γ-butyrolactone is known in the art. It can be prepared, for example, by the method of J. E. Livak et al., J. Am. Chem. Soc. 67, p.2218 (1945). Generally the process of the present invention includes the steps of mixing α-amino-γ-butyrolactone hydrobromide, one mole, with more than about 2 moles of pyridine in the presence of water as solvent, cooling to about 0° ± 5°C, adding about 1 to 1.25 moles of alkylchloroformate, allowing to stand at about 0° for a period of time sufficient for the reaction to go substantially to completion, warming to room temperature and recovering the product therefrom. Recovery of the product is easily accomplished by reducing the volume of the reaction mixture, e.g., by evaporation, and chilling in an ice bath to crystallize the product.

Experimental studies indicated that AP-28 produces a sedative effect, a slight hypnotic effect and an important anti-convulsant effect when administered to laboratory animals. The toxic level, as yet undetermined, is so high that toxicity is nearly negligible. When administered to humans in clinical studies the compound induced quiet, long-lasting sleep in insomniac patients with no apparent effects on awakening. An evident and lasting anxiety-relieving effect was observed in patients suffering from stress and anxiety together with an improvement in their neurovegatative disorders and in apparently normal subjects without causing daily drowsiness or torpor in the amounts administered. When administered to elileptics, AP-28 prevented or reduced the number of seizures. No adverse effects were observed.

1. ACUTE TOXICITY IN ANIMALS

AP-28 was administered to adult rats (Wistar-Morini Strain) of both sexes after fasting overnight. It was administered in an aqueous 1-percent suspension of tragacanth gum orally by gastric probe or intraperitoneally. The data in Table 1 show that:
 a. The $LD_0$ was more than 2 g/kg by either route of administration.
 b. The highest oral dose produced a sedative effect, but it did not cause the loss of the righting reflex; on the other hand, the sedative effect was obtained starting from the lowest intraperitoneal dose (a dose which was ineffective when given orally), and at 1 g/kg the loss of the righting reflex occurred; the duration of this effect was proportional to the size of the administered dose.
 c. The sedative and hypnotic effects were not long lasting and the animal returned to normal.

TABLE 1

| Dose, mg/kg | Died*/ treated | Acute Toxicity of AP-28 to the Rat Under hypnosis**/ treated | Remarks |
|---|---|---|---|
| Intraperitoneal | | | |
| 250 | 0/4 | 0/4 | Sedated for about 15 minutes |
| 500 | 0/4 | 0/4 | Sedated for about 20 minutes |
| 1000 | 0/4 | 4/4 | Under hypnosis for about 15 minutes |
| 1500 | 0/4 | 4/4 | Under hypnosis for about 30 minutes |
| 2000 | 0/4 | 4/4 | Under hypnosis for about 60 minutes |
| Oral*** | | | |
| 250 | 0/4 | 0/4 | No particular effect |
| 500 | 0/4 | 0/4 | As above |
| 1000 | 0/4 | 0/4 | Slightly sedated |
| 1500 | 0/4 | 0/4 | Sedated |
| 2000 | 0/4 | 0/4 | Very sedated |

*In 24 hours;
**Loss of the righting reflex;
***By gastric probe.

II. SUBACUTE TOXICITY IN ANIMALS

The acute toxicity studies showed that a dose of 500 mg/kg of AP-28 by oral administration did not cause any particular effect in the rat, but a dose of 1000 mg/kg produced a mild sedative effect. Accordingly, 8 rats were given 500 mg/kg daily for 6 consecutive days. No sedative effect or other abnormal symptoms were observed, showing that there was no tendency for AP-28 to accumulate in the organism.

III. SEDATIVE EFFECT ON PERFORMANCE

The sedative effect of AP-28 was demonstrated in the following experimental models: (a) the enhancement of the hypnotic effect of sodium pentobarbital in the mouse; (b) spontaneous mobility in the rat; and (c) the ability of the mouse to remain on a rolling bar.
a. Enhancement of the hypnotic effect Forty mg/kg of sodium pentobarbital was injected intraperitoneally into mice and note was taken of animals losing the righting reflex and for how long. Other mice received a preliminary treatment with AP-28 at a dosage of 250 and 500 mg/kg, intraperitoneally, and thereafter sodium pentobarbital was given to them. The hypnotic effect of sodium pentobarbital was markedly enhanced and its enhancement was greater with the 500 mg/kg dose of AP-28 than with the smaller one. The results are given in Table 2.

b. Spontaneous mobility

Several groups of four mice each were placed in an apparatus designed to provide a measure of spontaneous mobility by counting the number of interruptions of a light beam for a period of 10 minutes. After preliminary measurement of mobility, animals were injected with AP-28 (250 and 500 mg/kg) intraperitoneally. Control animals received saline solution. Ten minutes thereafter the measurement of mobility was repeated. Five groups of mice were used as controls and six other groups were treated with varying doses of AP-28. Table 3 shows that mobility had fallen to 71.4% of the original level in the control animals at the time of the second measurement, whereas in mice receiving 250 or 500 mg/kg of AP-28 it had fallen to 31.9% and 23.1% of the baseline values, respectively.

TABLE 2

Enhancing effect of AP-28 (I) on sodium pentobarbital (II) - induced sleep in the mouse

| Treatment | Dose mg/kg intraperitoneally | Animals under hypnosis/treated | Duration of hypnosis in minutes* (m ± SE) |
|---|---|---|---|
| II | 40 | 3/4 | 3.25 ± 3.4 |
| I + II | 250 + 40 | 4/4 | 52.5 ± 13 |
| I + II | 500 + 40 | 4/4 | 75.2 ± 21.6 |

*Arithmetic mean. The value zero was assigned to animals not losing the righting reflex.

TABLE 3

Influence of AP-28 on spontaneous mobility in the mouse

| Intraperitoneal treatment* | Mean number of crossings (± SE) | | Percent reduction at 2nd measurement |
|---|---|---|---|
| | Before treatment | After treatment | |
| Saline | 270.6 ± 24 | 194.4 ± 23 | 28.6 (5)** |
| AP-28, 250 mg/kg | 261.5 ± 25 | 84.1 ± 15 | 68.1 (6) |
| AP-28, 500 mg/kg | 229 ± 15 | 50.5 ± 5 | 76.9 (6) |

*The treatment was given immediately after the first measurement or 10 minutes before the secon measurement.
**In parentheses the number of the animal groups (4 animals per group)

c. Rotating bar test

Mice were trained to remain on a rotating bar for at least three minutes. A group of five of the trained mice were given an intraperitoneal injection of 250 mg/kg of AP-28 in a 1% suspension of tragacanth gum. Another group of five mice were given an intraperitoneal injection of 500 mg/kg of AP-28 in a 1% suspension of tragacanth gum. All control animals stayed on the bar for the 3 minutes. Only two out of the five treated mice receiving the 250 mg/kg succeeded in staying on the bar for 3 minutes but none of those receiving the 500 mg/kg dose were able to remain for 3 minutes.

IV. SEDATIVE EFFECT, PHYSIOLOGICAL

The sedative effect produced by AP-28 was much more similar to the effect of neuroleptic drugs than to that produced, for instance, by barbituric acid derivatives. This particular feature of the compound could be deduced from the influence the compound exerted on: (a) d-amphetamine toxicity to the mice kept in group, and (b) the response time of the avoidance reflex.

a. Antagonism towards d-amphetamine

Six groups of 4 mice each were treated with 5 mg/kg d-amphetamine sulfate by intraperitoneal administration. Six groups of 4 animals each received the same dose of d-amphetamine sulfate plus 250 mg/kg of AP-28 intraperitoneally 15 minutes after d-amphetamine sulfate; six more groups of four animals each received saline solution and served as control animals. Spontaneous mobility was observed in every animal according to the procedure described hereinbefore. The number of times each animal crossed the light beam throughout the 10-minute test was noted. As can be seen in Table 4, treatment with AP-28 did not prevent d-amphetamine from stimulating spontaneous mobility.

However, AP-28 did reduce mortality from d-amphetamine. The same amount of AP-28 as above was injected intraperitoneally. Then 10 minutes later, an intraperitoneal injection of 10 mg/kg of d-amphetamine sulfate was administered. Eight animals were used for this test and kept in one 25×20×14-cm cage in an air-conditioned environment (20°C, 60 percent humidity). All of the eight control animals died, whereas only five of the eight animals treated with AP-28 died. The AP-28 protected the animals from the effects of d-amphetamine and a marked reduction of mortality was obtained.

b. Avoidance Reflex

A conditioning cage was constructed of two chambers with free access between chambers. The floor of one compartment was electrified to make it possible to deliver a mild shock. Mice were conditioned by first giving a warning signal and then after a short period of time the shock was applied. Eventually the mice learned to leave the electrified compartment after the warning bell sounded and they were then judged to be conditioned. The average period of time, in this experiment, for control animals (4) to leave the compartment was 53.3 ±4.5 sec. Four conditioned mice were administered AP-28 intraperitoneally with 250 mg/kg and their time was 60.6 ± 3.9 sec. Four more conditioned mice treated with 500 mg/kg of AP-28 required 77.5 ± 2.7 sec. to clear the compartment.

TABLE 4

Influence of AP-28 on amphetamine - induced Hypermobility

| Intraperitoneal treatment | Mean number of crossings (± SE) in 10 minutes | Number of groups* |
|---|---|---|
| Saline | 229.8 ± 19 | 6 |
| d-amphetamine, 5 mg/kg | 657 ± 59 | 6 |
| Saline + saline** | 252.6 ± 13 | 6 |
| d-amphetamine + AP-28 | 836 ± 100 | 6 |

*Number of animal groups (4 animals per group)
**Ap-28 (or saline to controls) was given 15 minutes after d-amphetamine injection

TABLE 5

Protective Effect of AP-28 against Strychnine

| Pretreatment* | Died/treated | Animals with convulsions treated | Time of death** in minutes |
|---|---|---|---|
| None | 9/10 | 9/10 | 6 – 15 |
| AP-28 500 mg/kg os | 0/9 | 5/9 | No deaths |
| None | 8/8 | 8/8 | 7 – 12 |
| AP-28 250 mg/kg i.p. | 1/7 | 7/7 | 33 |
| AP-28 500 mg/kg i.p. | 0/8 | 3/8 | No deaths |

*Given 30 minutes before strychnine
**Extreme values

V. ANTI-CONVULSANT EFFECT

The anti-convulsant effect was determined by the extent to which AP-28 antagonized the convulsant effect produced by strychnine sulfate or by electroshock. A marked protective effect was observed in both methods.

a. Antagonism towards strychnine

This type of antagonism was evaluated in the mouse in three ways, namely: (1) protection from death from one hypodermic injection of strychnine: (2) evaluation of the $LD_{50}$ of strychnine in mice both treated and untreated with AP-28, and (3) influence on the time required to cause animals to die by slow intravenous perfusion of strychnine. The details of the experiments and the results obtained were as follows: (1) single oral 500 mg/kg doses of AP-28 protected all of the animals against the lethal effect of 1.2 mg/kg of strychnine sulfate in the mouse. Groups of six mice were used. The results are given in Table 5. (2) increasing amounts of strychnine sulfate were injected hypodermically. In two experiments 200 or 400 mg/kg of intraperitoneal AP-28 were given 30 minutes prior to strychnine injection and the $LD_{50}$ was calculated. The following results were obtained (95-percent confidence limits):

| | $LD_{50}$, mg/kg of Strychnine |
|---|---|
| CONTROL EXPERIMENTS | 0.83 (1.02–0.67) |
| PRETREATMENT WITH 200 mg/kg of AP-28 | 1.30 (1.36–1.03) |
| PRETREATMENT WITH 400 mg/kg of AP-28 | 1.60 (1.74–1.46) |

(3) continuous intravenous infusion at constant rate (0.4 ml/min) of a strychnine sulfate solution (26.66 mg/l) was carried out by injection through a tail vein into mice until they died. One group of animals received 500 mg/kg of AP-28 as preliminary treatment 15 minutes prior to the beginning of infusion. The mean infusion time to cause six control animals to die was 134 ± 3.2 seconds (mean ± SE). The mean infusion time required to obtain the same effect in animals pretreated with AP-28 was 210 ± 6.1 seconds.

In another experiment the infusion rate of strychnine was lowered to 0.25 ml/min. Under this condition, the mean infusion time was 246 ± 3.1 seconds in the case of controls (six animals) and 338 ± 24.3 seconds in that of treated animals.

When the same infusion rate as above was maintained and the amount of AP-28 was reduced to 250 mg/kg, the mean infusion time was 260 ± 13.4 seconds with control animals and 360 ± 21.2 seconds with treated animals.

b. Antagonism towards electroshock in the mouse

Electroshock was produced in mice through the application of ear electrodes. Stimulation parameters which could induce the maximal electroshock seizure (MES) were adopted. This was obtained by applying rectangular input shocks for 0.6 seconds. Each input lasted 0.4 ms and the input frequency was 25/sec. Phenobarbital sodium was used as the control substance. It was injected intraperitoneally 10 minutes prior to the MES. An amount of 250 mg/kg of AP-28 was injected by the same route as phenobarbital sodium. As shown in Table 6, AP-28 was as effective as phenobarbital sodium.

VI. INFLUENCE ON THE ELECTROMYOGRAM

Intraperitoneal injection of 500 mg/kg of AP-28 caused the electromyographic tracing to become flat in the rabbit with electrodes implanted in its cerebral cortex. That effect was similar to the effect caused by 30 mg/kg of intravenous phenobarbital sodium.

In the unrestrained cat with permanent electrodes implanted in the geniculate body, hippocampus, and cerebral cortex, the concomitatant recording of eye movements and neck muscle contractions after doses of 500 or 1000 mg/kg of AP-28 showed that sedation occurred without the electromyographic alterations which usually indicate sleep.

In cats having been conditioned to sleep for 8 hours from late morning, 250 and 350 mg/kg of AP-28 did not modify the total sleeping time, but reduced the number of cases of REM sleep and the overall length of the period of time spent by the animal in sleeping did not change, the period of time during which the animal sleep was characterized by slow waves was comparatively longer.

VII. PHARMACOLOGICAL ACTIVITY ON SYSTEMS OTHER THAN THE CNS

The effect of a single 500 mg/kg oral dose of AP-28 was determined on (a) diuresis in water-loaded rats, (b) choleresis, (c) the excretion rate of intravenously-injected bromosulfonphthalein in bile, (d) arterial blood pressure. No treatment caused any significant change in the above parameters except that the rate of urine excretion was slowed in water-loaded rats being treated with a daily dose of 500 mg/kg of oral AP-28 for 5 subsequent days.

TABLE 6

Protective Effect of AP-28 against Electroshock

| Treatment* | mg/kg | Number animals with | | |
|---|---|---|---|---|
| | | Clonic convulsions | Tonic convulsions | Died |
| Saline Solution | 1000 | 16(16)** | 16(16) | 6/16 |
| Phenobarbital Na | 40 | 8(8) | 0(8) | 0/8 |
| AP-28 | 250 | 8(8) | 0(8) | 0/8 |

*10 Minutes before electroshock
**In parentheses the number of treated animals

CLINICAL TRIALS

Clinical trials were performed on three groups of patients, partly hospitalized patients and partly outpatients. It was determined that the effect observed in the experimental pharmacological studies were useful in the treatment of humans as well.

1st Group

Seven patients complaining of insomnia were treated for a period of time varying from 5 to 15 days. The daily dose was 400–600 mg given as one dose at night. Patients slept quietly and for a long period of time and reported no blunting or grogginess of their minds when they woke up. The study demonstrated the ability of the drug to induce sleep.

2nd Group

Twelve patients reporting strain and anxiety (irritability, anxiety, apprehension), most of whom exhibited somatization and neurovegatative disorders of an anxiety-causing type, were treated with AP-28.

The dose levels used with these patients varied between 500 and 1500 mg/day, divided into two or three doses which were given during the day.

In all patients, except one, symptoms were attenuated and a reduction of their psychic stress was observed.

The tension-lowering effect seemed to be independent of the sedative effect and in no case somnolence, daily torpor or motive conceptual slowness were observed. No outpatient reported disorders or difficulty in carrying out his usual working activity.

3rd Group

Four patients suffering from essential epilepsy were treated for periods of time varying between 10 and 30 days with daily doses ranging from 0.500 to 1.500 g. During the observation period two patients had no fits, and the third patient showed a marked reduction of the number of fits. In the fourth patient it was possible to lower the anti-epileptic massive therapy he had been following for some time, and on which he was maintained throughout this study, by more than 50%.

In all of these patients improvement in their behavior and temper could be observed.

EXAMPLE 1

Preparation of AP-28

α-Amino-γ-butyrolactone hydrobromide was prepared by the method of Livak et al., cited above. A 130 g portion was dissolved in 1500 ml of water mixed with 136 g of pyridine. The mixture was cooled to 0°C in an ice and water bath and 100 g of n-butyl chloroformate was added with mixing. The mixture was stirred at 0°C for 2 hours and then was allowed to warm to 20°–22°C over a period of about 6 hours.

The reaction mixture thereby obtained was concentrated under reduced pressure to about 400 ml and was cooled to about 2°–3°C, producing a crystal crop of white, shining needles. The mixture was filtered and dried. The product, 119.6 g, had a melting point of 72°–73.5°C, titer 99.2%. The yield calculated on the α-amino-γ-butyrolactone hydrobromide was about 90%.

EXAMPLE 2

The experiment of Example 1 was repeated in all essential details except that isobutyl chloroformate was substituted for n-butyl chloroformate. A good yield of α-isobutoxycarbonyl-amino-γ-butyrolactone, m.p. 85°–86° was obtained.

The compound is administered to laboratory animals at a dose of about 500 mg/kg. The animals are sedated.

EXAMPLE 3

The experiment of Example 1 is repeated in all essential details except that isopropyl chloroformate is substituted for n-butyl chloroformate. A good yield of α-isopropoxycarbonyl-amino-γ-butyrolactone is obtained. It is administered to laboratory animals at a dose of about 500 mg/kg. The animals are sedated.

EXAMPLE 4

The experiment of Example 1 is repeated in all essential details except that n-pentyl chloroformate is substituted for n-butyl chloroformate. A good yield of α-n-pentylcarbonyl-amino-γ-butyrolactone is obtained. It is administered to laboratory animals at a dose of about 500 mg/kg. The animals are sedated.

I claim:

1. A method for treating animals in need of sedation by administering thereto orally or intraperitoneally a compound represented by the formula

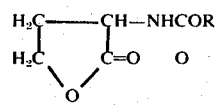

where R is alkyl of 3–5 carbon atoms, at a dosage of about 200 mg/kg to 2000 mg/kg.

2. The method of claim 1 wherein said compound is α-n-butoxycarbonyl-amino-γ-butyrolactone.

3. The method of claim 1 wherein R is alkyl of 3 carbon atoms.

4. The method of claim 1 wherein R is alkyl of 4 carbon atoms.

5. The method of claim 1 wherein R is alkyl of 5 carbon atoms.

* * * * *